United States Patent [19]
Thunberg

[11] Patent Number: 5,964,715
[45] Date of Patent: Oct. 12, 1999

[54] METHOD FOR MODIFYING AT LEAST ONE CALCULATION ALGORITHM IN A BIOPSY SYSTEM, AND BIOPSY SYSTEM OPERATING ACCORDING TO THE METHOD

[75] Inventor: Stefan Thunberg, Lidingö, Sweden

[73] Assignee: Siemens Elema AB, Solna, Sweden

[21] Appl. No.: 09/002,376

[22] Filed: Jan. 2, 1998

[30] Foreign Application Priority Data

Jan. 17, 1997 [SE] Sweden .................................. 9700117

[51] Int. Cl.[6] .................................................. A61B 10/00
[52] U.S. Cl. ........................ 600/562; 600/417; 378/37; 378/207
[58] Field of Search ................................... 600/562, 416, 600/417; 250/252.1; 378/37, 207

[56] References Cited

U.S. PATENT DOCUMENTS

| | | | |
|---|---|---|---|
| 4,655,716 | 4/1987 | Hoevel | 434/267 |
| 4,727,565 | 2/1988 | Ericson | 378/205 |
| 5,078,142 | 1/1992 | Siczek et al. | 128/653.1 |
| 5,095,499 | 3/1992 | Wentz | 378/37 |
| 5,240,011 | 8/1993 | Assa | 600/564 |
| 5,273,435 | 12/1993 | Jacobson | 434/267 |
| 5,359,637 | 10/1994 | Webber | 378/2 |
| 5,442,674 | 8/1995 | Picard et al. | 378/20 |
| 5,565,678 | 10/1996 | Manian | 250/252.1 |
| 5,584,292 | 12/1996 | Cheung | 128/653.1 |
| 5,712,890 | 1/1998 | Spivey et al. | 378/37 |
| 5,719,916 | 2/1998 | Nelson et al. | 378/207 |
| 5,805,665 | 9/1998 | Nelson et al. | 378/207 |
| 5,844,242 | 12/1998 | Jalink, Jr. et al. | 250/370.09 |

*Primary Examiner*—Cary O'Connor
*Assistant Examiner*—Charles Marmor, II
*Attorney, Agent, or Firm*—Hilt & Simpson

[57] ABSTRACT

In a method for modifying at least one calculation algorithm in a biopsy system and a biopsy system operating according to the method, a phantom is placed in a specific position on an object table in a biopsy system and the phantom is irradiated with penetrating radiation from at least two angles to produce at least two images. The phantom contains markers at exact positions, and the calculation algorithm can be modified on the basis of information on the known positions of the markers and image information in the two exposures.

6 Claims, 4 Drawing Sheets

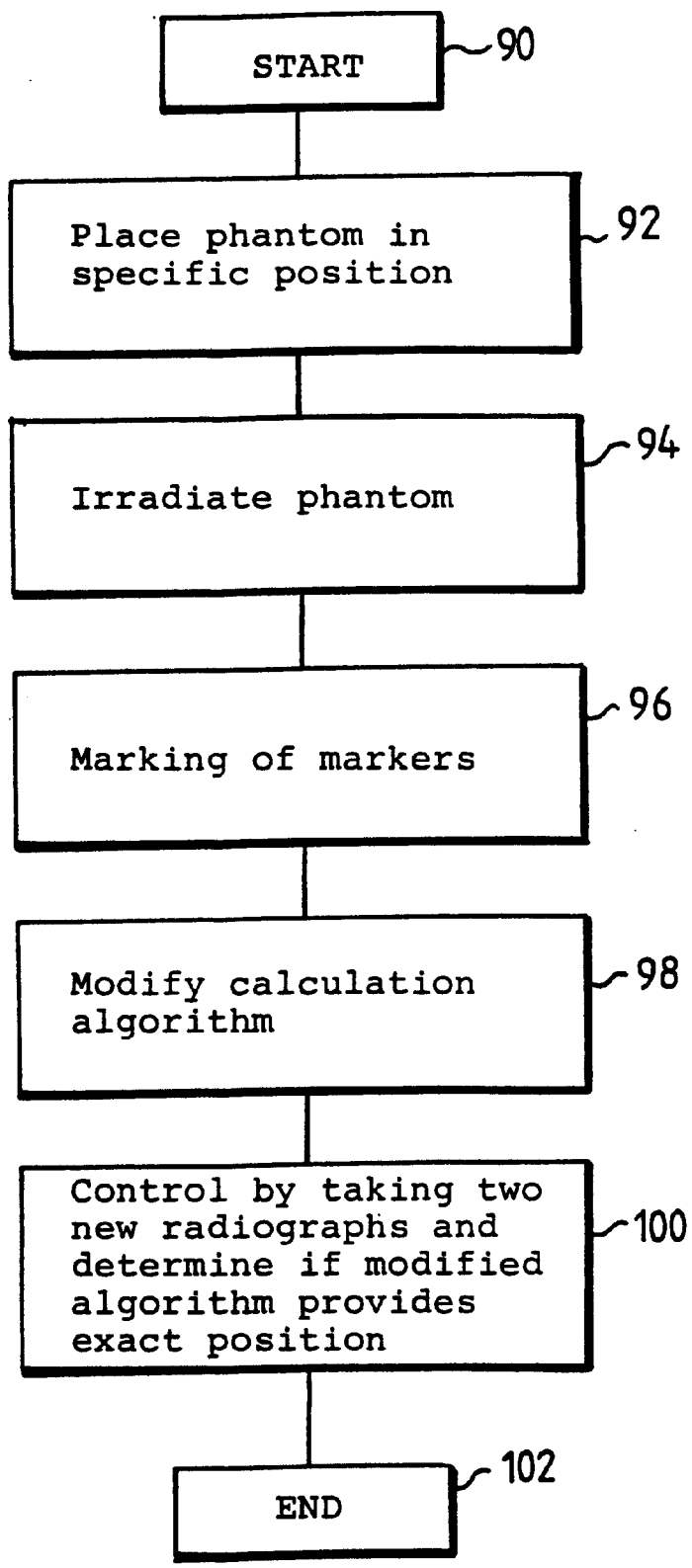

METHOD FOR MODIFYING AT LEAST ONE CALCULATION ALGORITHM IN A BIOPSY SYSTEM, AND BIOPSY SYSTEM OPERATING ACCORDING TO THE METHOD

BACKGROUND OF THE INVENTION

1. Field of the Invention

The present invention relates to a method for modifying at least one calculation algorithm in a biopsy system, the calculation algorithm having an influence on the determination of the position of a cell or tissue-sampling area in a stereotactic biopsy procedure.

2. Description of the Prior Art

The present invention also relates to a stereotactic biopsy system for examining the breast, the female breast in particular, of the type having a mammography apparatus, a biopsy apparatus and a calculation unit for stereotactic calculation of the position of a cell or tissue-sampling area.

Swedish Patent Application, SE-8306243-0, discloses a method for locating the position of a three-dimensional point in an object, e.g. a female breast, in conjunction with x-ray irradiation of that object. This is achieved by fixing the object in a predefined position, whereupon it is exposed with an exposure apparatus from two angles on either side of a center line perpendicular to the image plane, so that a first image and a second image are obtained. The two-dimensional position of the sought point in the two images is then determined in relation to an index in each of the images. The coordinates of the point in relation to the index are processed to obtain control signals for setting an aiming instrument, with an insertion instrument, to the desired point in the object.

U.S. Pat. No. 5,240,011 discloses a motor-driven unit for use in a biopsy system for automatic positioning of a biopsy needle in order to allow insertion of the needle to a previously identified point of interest in the breast of a patient.

Even though most contemporary stereotactic mammographic biopsies are made using film, systems incorporating digital image detectors have been introduced for mammography in recent years.

Extreme accuracy is required in all types of stereotactic biopsies in determining the x, y, z coordinates of a cell or tissue-sampling area in which a suspected tumor or some other tissue change has been discovered. The physician needs to be absolutely certain that a specimen has been taken from the interesting (suspicious) area. Locations are determined with a calculation algorithm which includes e.g. the apparatus constants of the system. If this very high degree of accuracy is to be achieved, very exact values for apparatus constants must be used, which truly correspond to system realities. Examples of apparatus constants are the x-ray tube's angle of inclination, the x-ray focus-detector distance, the distance to the axis of rotation, the table top-to-focus distance and the table top-to-detector distance.

Installation of a stereotactic biopsy unit is often a very time-consuming and patience-demanding procedure, since calibration of the tube's angle of inclination (an apparatus constant) is often necessary. Calibration is also performed during the manufacture and service of systems, especially when usage-induced wear can affect the apparatus constants which have been previously set.

SUMMARY OF THE INVENTION

An objective of the present invention is to provide a biopsy system and method wherein the aforesaid problems are easily accommodated. This is achieved in a method for determining at least one apparatus constant in a biopsy system according to the present invention, and in a biopsy system employing this method.

The method according to the present invention is intended for modification of at least one calculation algorithm in a biopsy system, the calculation algorithm having an influence on determination of the position of a cell or tissue-sampling area in stereotactic biopsy. The method includes the following steps of placing a phantom, made of a stable radiotransparent material in which a specific number of radiopaque markers are arranged at known, predetermined positions, in a specific position on an object table, irradiating the phantom with penetrating radiation from at least two beam angles so at least two images are obtained, and modifying the calculation algorithm on the basis of the known positions of the markers and information in the images.

In principle, the method can be considered as being based on a reversal of methods employing conventional techniques. Instead of using calculation algorithms to establish exact values for apparatus constants, which must be calibrated on the equipment with great care and with a considerable expenditure of time, the apparatus constants in the inventive method are allowed to be somewhat inexact, and the calculation algorithm is modified so that determination of the position of the cell or tissue-sampling area compensates for deviations in apparatus constants. Modification can be performed automatically, and the entire calculation algorithm can, in principle, be determined from information in the images as to the position of the markers and other image information. The salient feature is that the space in which a cell specimen is to be taken is accurately defined by the algorithm.

Preferably the phantom's fixed position on the object table is determined by a radiograph taken immediately above and perpendicular to the phantom.

The biopsy system according to the present invention is intended for examination of the breast, the female breast in particular, and includes a mammography apparatus, a biopsy apparatus and a calculation unit for stereotactic calculation of the position of a cell or tissue-sampling area, the calculation being devised to modify at least one calculation algorithm for the biopsy system in accordance with the above-described method on the basis of stereotactic images of a phantom made of a stable, radio-transparent material in which a specific number of radiopaque markers are arranged at known, predefined positions.

Preferably the biopsy system contains a digital image-generating unit, e.g. a CCD system.

DESCRIPTION OF THE DRAWINGS

FIG. 5 is a flow chart illustrating a method according to the present invention for modifying at least one calculation algorithm for a biopsy system.

DESCRIPTION OF THE PREFERRED EMBODIMENTS

In a stereotactic biopsy system, the positions of cell-sampling areas is determined with calculation algorithms. Calculation algorithms contain values for various apparatus constants.

Figure 1:
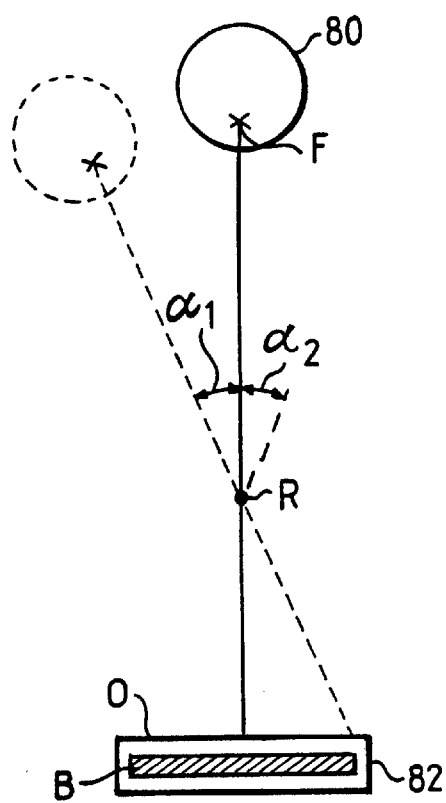
FIG. 1 illustrates various apparatus constants associated with most known systems and with the inventive system.

FIG. 1 is a drawing which elucidates and explains various apparatus constants. The reference number 80 designates a schematically rendered x-ray tube in a biopsy system according to FIGS. 3 or 4 below, and 82 designates the object table in the same system. The letter F designates the focus of the x-ray tube 80. The letter R designates the x-ray tube's axis of rotation, i.e. the axis around which the tube can be rotated. The letter 0 designates the top of the object table 82. The letter B designates the image-generating unit (either a film cassette or CCD system). $\alpha_1$ and $\alpha_2$ respectively designate the two beam angles in relation to the centerline, $\alpha_1$ should be as large as $\alpha_2$. The different apparatus constants used in the calculation algorithm should be one or more of the following:

1. The distance between the focus F and the axis of rotation R;
2. The distance between the focus F and the top of the object table O;
3. The distance between the focus F and the image-generating unit B;
4. The angles $\alpha_1$ and $\alpha_2$
5. The distance between the top of the object table O and the image-generating unit B;
6. The distance between the top of the object table O and the axis of rotation R; and
7. The distance between the image-generating unit B and the axis of rotation R.

These apparatus constants all vary considerably from one type of apparatus to another. Manufacturing tolerances apply to the same type of apparatus.

Figure 2:
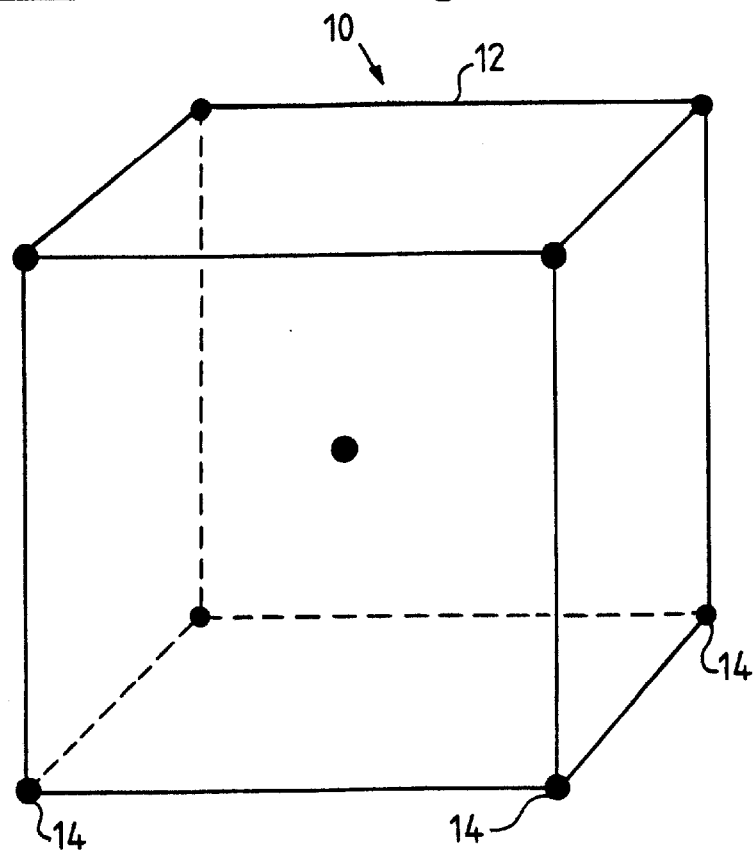
FIG. 2 is a perspective view of a first embodiment of a known phantom.

FIG. 2 is a perspective view of a known phantom 10, the phantom 10 being intended for use in modifying calculation algorithms for stereotactic biopsy systems. The illustrated phantom 10 is in the shape of a cube 12 but could be devised as any kind of rectilinear block. The phantom 10 is made of a stable material which is transparent to x-rays in relation to the markers 14. The phantom 10 contains a number (nine in this example) of markers 14 arranged in the phantom 10 at known, predefined positions, in this example one marker 14 in each corner and one marker 14 in the center. The markers 14 are made of a material which absorbs x-rays to a greater extent than the cube 12. The radio-transparent material for the biopsy system consists of e.g. thick bakelite, aluminum, stable plastic or plexiglass. The reason for this choice of material is to keep the markers 14 from changing their position in the phantom 10 and to promote their distinct, high-contrast rendering in radiographs. The markers 14 are made of metal, e.g. lead or steel, and are preferably less than 2 mm in diameter. The smaller the markers 14, the greater the accuracy in determining their positions, thereby improving modification of the calculation algorithm. In the example shown in FIG. 2, the phantom 10 has nine markers 14, but a different number could naturally be used. A suitable number is three to nine markers 14. With this range there are enough markers 14 to supply the desired image information but not too many as to make it hard to distinguish them in the radiographs. In the example shown in FIG. 2, the markers 14 are asymmetrically arranged in the phantom 14, but they can alternatively be arranged symmetrically. The fact that the phantom 10 has the shape of a rectilinear block, a cube in this instance, makes it easier to place the phantom 10 at a specific position on the object table. The markers 14 do not need to be inside the phantom 10, as in FIG. 2, but one or more or all of the markers 14 can be embedded in the surface of the phantom 10. For example, the phantom 10 could have three markers 14 in a bottom surface to permit identification of position on the object table from the radiographs and one marker 14 in an upper surface, thereby yielding maximum displacement of position in the two images.

In the example shown in FIG. 2 the phantom 10 consists of a solid object, but this need not be the case. The phantom 10 could e.g. consist of a hollowed-out rectilinear block or a drilled-through block containing simulated markers.

The positions of the markers 14 in the phantom 10 can be determined in accurately calibrated equipment, i.e. each manufactured phantom 10 receives individually arrayed markers 14. The positions of the markers 14 can also be set by accurate fabrication in which all manufactured phantoms 10 are identical.

Figure 3:
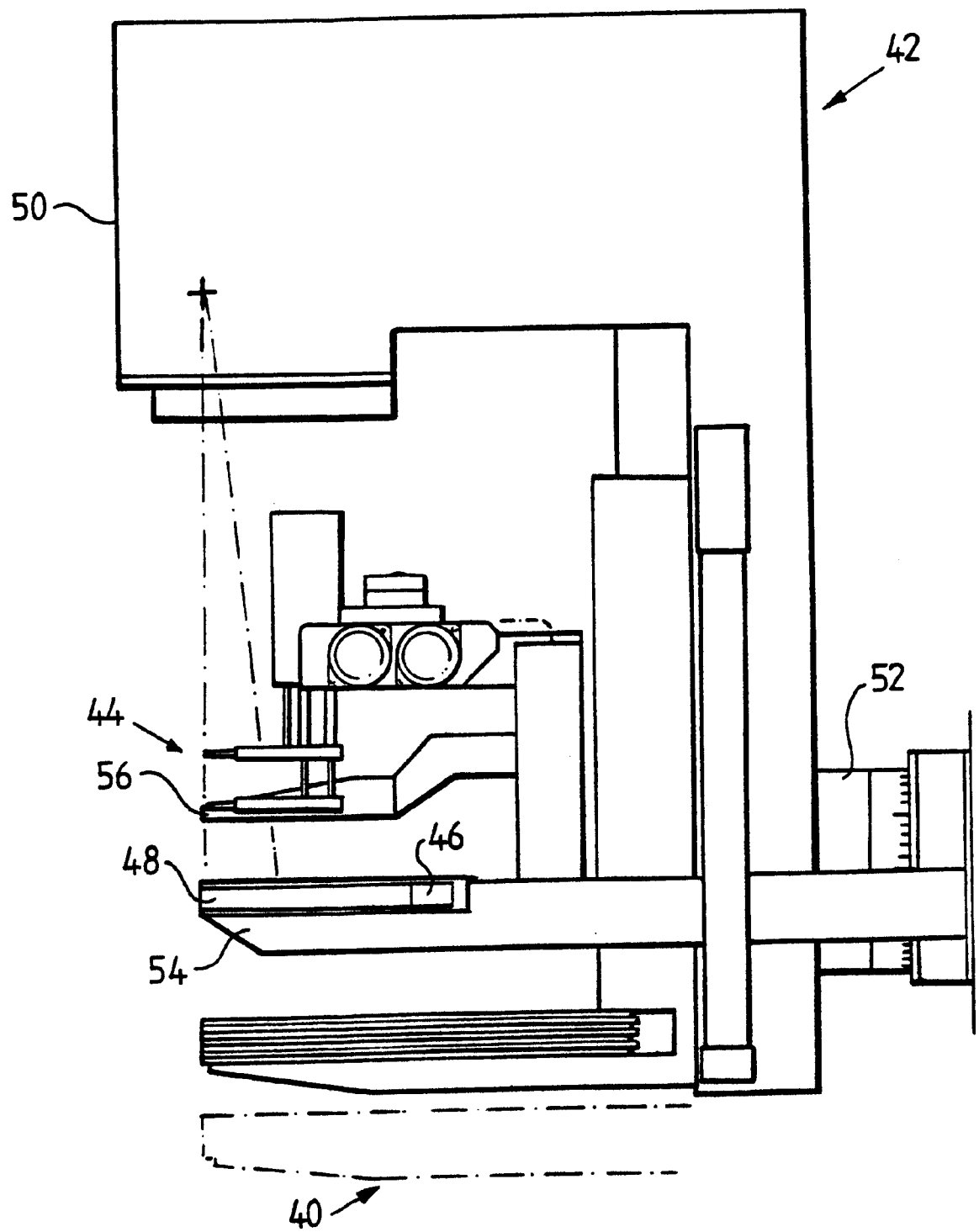
FIG. 3 is a lateral view of a first embodiment of the biopsy system according to the present invention.

FIG. 3 shows a lateral view of a first embodiment of the biopsy system 40 according to the present invention. The illustrated biopsy system 40 is intended for digital stereotaxy for examination and specimen collection from suspicious areas displaying tissue changes, particularly in the female breast. The biopsy system 40 includes a mammography apparatus 42, a biopsy apparatus 44 and a calculation unit 46 for stereotactic determination of the location of a suspected tumor or a suspicious area. The biopsy system 40 also contains an image-generating unit 48 formed by a CCD system 48 (charge-coupled device) or employing some other digital technology. In the illustrated example, the calculation unit 46 and CCD system 48 are physically part of the same unit. The biopsy apparatus 44 is a separate unit, which can be connected to the mammography apparatus 42, and contains, in the illustrated example, both the calculation unit 46 and CCD system 48. The mammography apparatus 42 is a conventional mammography apparatus and contains an x-ray tube 50 which can be rotated around an axis 52. In the illustrated example, the biopsy apparatus 44 also contains an arm 54 on which a cassette holder for the CCD system 48 and the calculation unit 46 are arranged. The biopsy apparatus 44 further contains a compression plate 56 arranged above the arm 54. The compression plate 56 is vertically movable and has a opening, e.g. 50×40 mm, to permit the insertion of e.g. a biopsy needle into a breast (not shown) compressed by the compression plate 56 and arm 54. Dashed lines indicate the path of the beam from the x-ray-emitting tube 50.

The calculation unit 46 is devised to modify at least one calculation algorithm for the biopsy system 40 on the basis of stereotactic images of a phantom according to the present invention (cf. FIGS. 1–2). Modification may be necessary especially in conjunction with fabrication, installation and service.

When modification is to be performed according to the present invention, a phantom 10 is accordingly placed in a specific position on the object table (corresponding to the arm 54 and CCD system 48 in the example shown in FIG. 3). The exact position of the phantom 10 on the object table 54 (i.e., on the CCD system 48) can be determined with a vertical radiograph taken immediately above the phantom 10, and the position can be related to the image area of the CCD system 48. An alternative to this is to place the phantom 10 against a stop or the like arranged on the object table 54 so that the starting point is fully known. When the phantom 10 has been placed in the specific position on the object table 54, the phantom 10 is irradiated by the x-ray tube 50 from two angles on either side of a centerline perpendicular to the image plane, so that two radiographs are obtained. The calculation unit 46 then modifies the calculation algorithm, according to image information and the known positions of the markers 14 in the phantom 10, so that the calculation algorithm supplies the exact positions.

The calculation unit 46 employs the exact marker positions and information in images of the phantom 10 to modify the calculation algorithms used in stereotactic biopsy for establishing the x, y, z coordinates for a cell or tissue-sampling area. This means that each stereotactic biopsy system receives individually calibrated calculation algorithms, thereby ensuring accuracy and simplifying installation.

The system can then be put into service. A patient's breast is placed in the compressed state in the biopsy system 40 in a known manner. The breast is then irradiated by the x-ray tube 50 from two angles on either side of a centerline perpendicular to the image plane, so that two images are obtained. These two images are detected by the image-generating unit, i.e., the CCD system 48. The calculation unit 46 then uses the modified calculation algorithm and information in images of the breast to determine the x, y, z coordinates of the cell or tissue-sampling area. These x, y, z coordinates are subsequently employed for inserting a biopsy needle into a cell or tissue-sampling area and obtaining a tissue specimen.

In the example shown in FIG. 3, the biopsy apparatus 44 incorporates e.g. the calculation unit 46 and the CCD system 48. This need not be the case. The calculation unit 46 and CCD system 48 can be physically separate units. The calculation unit 46 e.g. can consist of software run on e.g. a personal computer connected to the mammography apparatus 42. An additional advantage of the CCD system 48 is that it can be devised to fit into a cassette holder intended for a conventional film cassette. This means that an "old" biopsy system can be easily modified.

Figure 4:
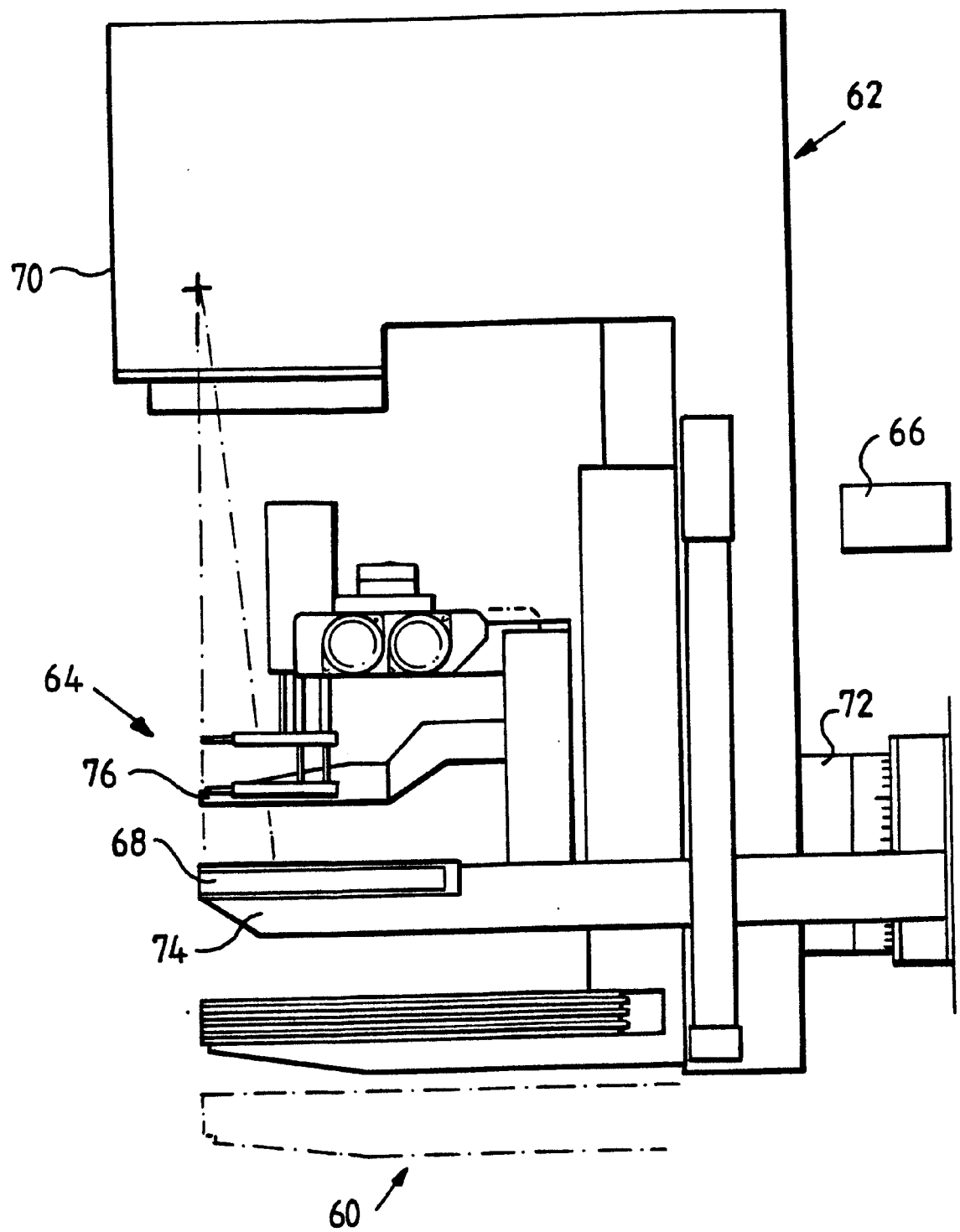
FIG. 4 is a lateral view of a second embodiment of the biopsy system according to the present invention.

FIG. 4 shows a lateral view of a second embodiment of the biopsy system 60 according to the present invention. The illustrated biopsy system 60 is intended for stereotaxy with film for examination of the breast, the female breast in particular. The biopsy system 60 includes a mammography apparatus 62, a biopsy apparatus 64 and a calculation unit 66 for stereotactic calculation of the position of a cell or tissue-sampling area. As FIG. 4 schematically shows, the calculation unit 66 is a separate apparatus. The biopsy system 60 also contains an image-generating unit formed by a film cassette 68. The mammography apparatus 62 is a conventional mammography apparatus and contains an x-ray tube 70 which rotates around an axis 72. The biopsy apparatus 64 has an arm 74 on which a cassette holder for the film cassette 68 is arranged. The biopsy apparatus 64 further contains a compression plate 76 arranged above the arm 74. The compression plate 76 is vertically movable and has a opening, e.g. 50×40 mm, to permit insertion of e.g. a biopsy needle into a breast (not shown) compressed by the compression plate 76 and the arm 74.

Modification of the calculation algorithm in the biopsy system 60 according to the present invention is performed in essentially the same way as described for FIG. 3. One major difference is that image registration is accomplished with a film cassette that supplies ordinary radiographs. This means exposed film is fixed in the calculation unit 66, and the calculation unit 66 then modifies the calculation algorithms used in determining the x, y, z coordinates of a cell or tissue-sampling area in stereotactic biopsy.

FIG. 5 is a flow chart showing a method according to the present invention for modifying at least one calculation algorithm in a biopsy system, the calculation algorithm having an influence on determination of the position of cell or tissue-sampling areas in stereotactic biopsy when the system is used. The method starts in step 90. In step 92, a phantom, made of a stable radio-transparent material in which a specific number of radiopaque markers are arranged at known, predefined positions, is then placed in a specific position on an object table. In step 94, the phantom is irradiated from two angles to yield two images. The method continues in step 96 wherein the markers are manually or automatically marked. The calculation algorithm is modified in step 98. In step 100, new radiographs are taken, and the modified calculation algorithm is checked. New modifications may then be made until the most recently modified algorithm identifies the exact position of the markers. The method is then concluded in step 102.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining at least one calculation algorithm in a biopsy system, said calculation algorithm having an influence on a determination of a position of an area of interest in a stereotactic biopsy procedure, said method comprising the steps of:

providing a phantom composed of a stable, radio transparent material and containing a plurality of radiopaque markers respectively disposed at predetermined positions in said phantom;

placing said phantom in a known position on an object table;

irradiating said phantom with penetrating radiation from two different angles and thereby obtaining two radiological images of said phantom; and modifying a calculation algorithm used for identifying a position of a region of interest in a subject to be subsequently irradiated, employing information relating to the positions of said markers in said radiographic images and other image information contained in said radiological images.

2. A method as claimed in claim 1 wherein the step of positioning said phantom in a known position on an object table comprises identifying a known position for said phantom on said object table by obtaining a vertical radiographic image of said phantom from immediately above said phantom.

3. A biopsy system for examining a breast, comprising:

mammography exposure apparatus for obtaining radiographic exposures;

a biopsy apparatus for conducting a biopsy to obtain a tissue sample from a predetermined location in a subject using said radiological exposures for positioning said biopsy apparatus;

a phantom composed of a stable, radio-transparent material and containing a plurality of radiopaque markers disposed at respective, predetermined positions in said phantom;

means for placing said phantom on an object table at a known position;

means for operating said mammography apparatus for obtaining two radiographic images of said phantom at two different angles; and calculation means for calculating the position of a tissue sample to be taken based on a calculation algorithm and including means for modifying said calculation algorithm dependent on said radiographic images of said phantom.

4. A biopsy system as claimed in claim 3 wherein said calculation means comprises means for modifying said calculation algorithm for modifying a calculation of the position of said tissue sample.

5. A biopsy system as claimed in claim 3 wherein said mammography apparatus includes means for generating a digital image.

6. A biopsy system as claimed in claim 5 wherein said means for generating a digital image comprises a CCD system.

* * * * *